United States Patent [19]

Stroppolo et al.

[11] Patent Number: 5,807,894
[45] Date of Patent: Sep. 15, 1998

[54] SYRUP CONTAINING N-ACETYL-CYSTEINE

[75] Inventors: Federico Stroppolo, Pregassona, Switzerland; Daniele Bonadeo, Varese, Italy; Alessandro Saudino, Muralto, Switzerland; Annibale Gazzaniga, Rescaldina, Italy

[73] Assignee: Zambon Group S.p.A., Milan, Italy

[21] Appl. No.: 867,923

[22] Filed: Jun. 3, 1997

Related U.S. Application Data

[63] Continuation of Ser. No. 424,539, filed as PCT/EP93/03280, Nov. 23, 1993 published as WO/94/12108, Jun. 9, 1994, abandoned.

[30] Foreign Application Priority Data

Dec. 2, 1992 [IT] Italy .................................. MI92A2758

[51] Int. Cl.$^6$ .................................................. A61K 31/195
[52] U.S. Cl. .......................... 514/562; 514/970; 514/974; 424/400
[58] Field of Search ..................... 514/970, 562, 514/974; 424/400

[56] References Cited

U.S. PATENT DOCUMENTS 5,064,640  11/1991  Kleber et al. .............................. 424/52
5,401,514  3/1995   Juch et al. ................................ 424/465

FOREIGN PATENT DOCUMENTS 0 340662    11/1989  European Pat. Off. .
0 465921 A1 1/1992   European Pat. Off. .

OTHER PUBLICATIONS

Int. Pharm. Abs. 00118589: 23–07126 (1984), Thielens.
WPIDS Abstract 89–325938 (1989), Lualdi.

*Primary Examiner*—Russell Travers
*Assistant Examiner*—M. Moezie
*Attorney, Agent, or Firm*—Nikaido, Marmelstein Oram & Murray LLP

[57] ABSTRACT

A syrup containing N-acetyl-cysteine, stable for at least two years, having pleasant taste and smell, consists of an aqueous solution of NAC, a sweetening agent and a thickening agent. The solution can also contain a flavoring agent and a preservative. The pH is between 5 and 8.

4 Claims, No Drawings

SYRUP CONTAINING N-ACETYL-CYSTEINE

This application is a continuation of application Ser. No. 08/424,539, filed Jul. 25, 1995, now abandoned, which application is a 371 of PCT/EP93/03280 filed Nov. 23, 1993.

The present invention relates to a composition in the form of a syrup containing N-acetyl-cysteine as active ingredient.

N-acetyl-cysteine (hereinafter briefly referred to as NAC) is a compound endowed with several useful pharmacological properties, making it a widely used drug.

In the treatment of cold diseases, NAC showed to be useful thanks to its mucolytic properties.

One of the pharmaceutical forms largely used in the therapy of cold diseases is syrup, particularly suitable also for pediatric use.

NAC is available in several pharmaceutical forms, however the high reactivity of the molecule, the relative instability and the characteristic sulphureous smell and taste make extremely troublesome the achievement of liquid forms for oral use which are time-stable and with a good palatability.

The preparation of a syrup provides, practically in all the cases, the use of a disaccharide (sucrose) or of a simple sugar as a sweetening and thickening agent of the aqueous solution of the drug. However, the interaction of NAC with sugars gives to the solution an unacceptable brown colouring and the titre of NAC decreases.

Thus, it is not possible to leave NAC in solution for a long time in the presence of sucrose.

Similarly, the reactions giving brown colour and causing bad smell take place also between NAC and the monosaccharides whose use is described in the French patent application No. 2631831 in the name of Calco Anstalt.

As far as we know, the only syrup formulation containing NAC on the market consists in a composition to be prepared at the moment of use by dissolution in water of a granulate.

After preparation, the extemporaneous syrup must be used within 3 weeks.

We have now surprisingly found that it is possible to prepare a time-stable NAC syrup having a pleasant taste without using sugars. Therefore, object of the present invention is a composition in the form of a syrup containing (each 100 ml):

| | |
|---|---|
| N-acetyl-cysteine | 2–4.2 g/100 ml |
| a sweetening agent | 0.02–0.3 g/100 ml |
| a thickening agent selected among: | |
| sodium carboxymethylcellulose and hydroxypropylmethylcellulose or mixtures thereof | 0.1–4 g/100 ml |
| and optionally: | |
| a flavouring agent | 0.1–0.4 g/100 ml |
| a preservative | 0.05–0.5 g/100 ml |
| and further | |
| water q.s. to 100 ml | |
| pH being settled within the interval 5–8. | |

The above solution results to be stable in a closed bottle under inert gas for at least 2 years under environmental conditions. When the bottle is opened, the solution shows to have a pleasant taste and to be free from bad smells; NAC maintains the initial titre and the open syrup results to be stable for at least 5 weeks.

For sweetening agent we mean a substance able to give a sweet taste to the solution but wich does not contain sugars. Specific examples of sweetening agents are saccharin, sodium saccharin and cyclamates or mixtures thereof.

The amount of sweetening agent will be the minimum amount sufficient to give a pleasant taste to the solution.

The thickening agent is selected among sodium carboxymethylcellulose methylcellulose and hydroxypropylmethylcellulose or mixtures thereof. Surprisingly, these substances showed to be compatible with NAC and to be able to give to the solution a thickness suitable for the usual palatability of a syrup.

To these three base components (NAC, sweetening agent and thickening agent) water can be added up to the selected volume, by optionally rectifying the resultant pH so that it is maintained within the interval from 5 to 8. Preferably, pH will be from 6.5 to 7.

The syrup could also, but not necessarily, contain a flavoring agent in order to improve the palatability, especially for pediatric use.

Since the syrup is generally manufactured in absence of asepsis, pharmacopoeiae require the compulsory presence of a preservative. The preservative is further required to assure the microbiological quality during the time of use by the patient.

In this case, preservatives selected among sodium benzoate, methyl 4-hydroxybenzoate, propyl 4-hydroxybenzoate and mixtures thereof will be preferably used.

With the double function of preservative and of metal chelating agent also sodium EDTA could be used in addition to or in partial substitution of the above preservatives.

The preparation of the syrup according to the present invention is carried out under inert gas by simple dissolution of the substances in the predetermined amount of water.

The resultant solution is shared into multidose bottles or in single-dose containers.

The packaging of multi-dose bottles could provide the contemporaneous supplying of a graduated measure for the correct dosage of the single doses for grown-up people (for example 10 ml) or for children (for example 5 ml).

In order to better illustrate the present invention the following examples are now given.

EXAMPLE 1

10 liters of a syrup containing (each 100 ml):

| | |
|---|---|
| NAC | 2.1 g |
| Saccharin | 0.04 g |
| Sodium carboxymethylcellulose | 0.2 g |
| Sodium benzoate | 0.15 g |
| Sodium edetate | 0.1 g |
| Raspberry flavour | 0.25 g |
| Water q.s. to 100 ml | | were prepared by simple dissolution of the substances in purified and de-aerated water under nitrogen atmosphere.

The pH of the resultant solution was rectified to the correct value 6.5 by addition of sodium hydroxide.

The solution was shared at the rate of 150 ml/bottle.

The bottles were stored for 2 years at room temperature.

After this period, the titre of NAC resulted to be higher than 95% of the initial one.

Such a titre resulted to be higher than 90% of the initial one also after 5 weeks from the opening of the bottle.

The syrup, also after 2 years of storage, showed to have a pleasant taste and smell and a good general palatability.

EXAMPLE 2

10 l of a syrup having the following composition (each 100 ml):

| | |
|---|---|
| NAC | 2.1 g |
| Sodium saccharin | 0.04 g |
| Hydroxypropylmethylcellulose | 0.2 g |
| Methyl 4-hydroxybenzoate | 0.1 g |
| Sodium edetate | 0.1 g |
| Apricot flavour | 0.1 g |
| Water q.s. to 100 ml | | were prepared by dispersion of hydroxypropylmethylcellulose in a part of boiling water which was cooled to room temperature. After hydration of hydroxypropylmethylcellulose, it was poured into a solution obtained by dissolving all the remaining substances in purified and de-aerated water, under nitrogen atmosphere.

The pH of the solution was rectified to pH 6.5 with sodium hydroxide.

The solution was shared into single-dose sachets of 10 ml each containing about 200 mg of NAC.

EXAMPLE 3

10 l of a syrup having the following composition (each 100 ml):

| | |
|---|---|
| NAC | 2.1 g |
| Sodium saccharin | 0.04 g |
| Hydroxypropylmethylcellulose | 0.2 g |
| Sodium edetate | 0.1 g |
| Apricot flavour | 0.1 g |
| Water q.s. to 100 ml | | were prepared by dispersion of hydroxypropylmethylcellulose in a part of boiling water which was cooled to room temperature. After hydration of hydroxypropylmethylcellulose, it was poured into a solution obtained by dissolving all the remaining substances in purified and de-aerated water, under nitrogen atmosphere.

The pH of the solution was rectified to pH 6.5 with sodium hydroxide.

The solution was shared into single-dose glass vials of 10 ml with rubber stopper each containing about 200 mg of NAC.

EXAMPLE 4

By working as described in Example 1, 10 l of syrup having the following composition (each 100 ml) were prepared:

| | |
|---|---|
| NAC | 4.2 g |
| Sodium saccharin | 0.08 g |
| Sodium carboxymethylcellulose | 0.20 g |
| Sodium benzoate | 0.15 g |
| Sodium edetate | 0.10 g |
| Raspberry flavour | 0.4 g |
| Water q.s. to 100 ml | |

The pH of the solution was rectified to pH 6.5 with sodium hydroxide.

The solution was shared into bottles at the rate of 150 ml each bottle.

EXAMPLE 5

By working as described in Example 2, 10 l of syrup having the following composition (each 100 ml) were prepared:

| | |
|---|---|
| NAC | 2.10 g |
| Saccharin | 0.04 g |
| Hydroxypropylmethylcellulose | 0.40 g |
| Methyl 4-hydroxybenzoate | 0.10 g |
| Banana flavour | 0.4 g |
| Water q.s. to 100 ml | |

The pH of the solution was rectified to pH 7 with sodium hydroxide. The solution was shared into bottles at the rate of 450 ml each bottle.

We claim:

1. A composition in the form of a syrup containing in each 100 ml:

| | |
|---|---|
| N-acetyl-cysteine | 2–4.2 g/100 ml |
| a sweetening agent | 0.02–0.3 g/100 ml |
| a thickening agent selected among: | |
| sodium carboxymethylcellulose and hydroxypropylmethylcellulose or mixtures thereof | 0.1–4 g/100 ml | and optionally:

| | |
|---|---|
| a flavouring agent | 0.1–0.4 g/100 ml |
| a preservative | 0.05–0.5 g/100 ml | and further water q.s. to 100 ml, and having a pH being within the interval 5–8.

2. A composition according to claim 1 wherein the sweetening agent is selected among saccharin, sodium saccharin, cyclamates or mixtures thereof.

3. A composition according to claim 1 wherein the preservative is selected among sodium edetate, sodium benzoate, methyl 4-hydroxybenzoate, propyl 4-hydroxybenzoate and mixtures thereof.

4. A composition according to claim 1 wherein the pH is between 6.5 and 7.

* * * * *